United States Patent [19]

Leggett et al.

[11] Patent Number: 5,214,952
[45] Date of Patent: Jun. 1, 1993

[54] CALIBRATION FOR ULTRA HIGH PURITY GAS ANALYSIS

[75] Inventors: Gregory H. Leggett, Sanborn; Michael H. Sonricker, North Tonawanda, both of N.Y.

[73] Assignee: Praxair Technology, Inc., Danbury, Conn.

[21] Appl. No.: 745,697

[22] Filed: Aug. 16, 1991

[51] Int. Cl.$^5$ ............................................. G01D 18/00
[52] U.S. Cl. ..................................... 73/1 G; 73/31.03
[58] Field of Search ..................... 73/1 G, 31.02, 31.03

[56] References Cited

U.S. PATENT DOCUMENTS

| | | | |
|---|---|---|---|
| 3,242,715 | 3/1966 | Hübner | 73/1 G |
| 3,247,702 | 4/1966 | Houser et al. | 73/1 G |
| 3,359,784 | 12/1967 | Jorre et al. | 73/1 G |
| 3,533,272 | 10/1970 | Dahms | 73/1 G X |
| 3,776,023 | 12/1973 | Budd et al. | 73/1 G |
| 3,924,442 | 12/1975 | Kerho et al. | 73/1 G X |
| 3,976,450 | 8/1976 | Marcote et al. | 73/1 G X |
| 4,150,495 | 4/1979 | Stern | 73/1 G X |
| 4,290,296 | 9/1981 | Bredeweg et al. | 73/1 G |
| 4,314,344 | 2/1982 | Johns et al. | 364/571.05 X |
| 4,856,352 | 8/1989 | Daum et al. | 73/1 G X |
| 5,053,200 | 10/1991 | Schoeffer et al. | 73/1 G X |

FOREIGN PATENT DOCUMENTS 0370150 5/1990 European Pat. Off. .
0370151 5/1990 European Pat. Off. .

OTHER PUBLICATIONS

"Construction and Operation of a Simple Exponential Dilution Flask for Calibration of Gas Chromatographic Detectors", H. P. Williams et al, Journal of Gas Chromatography, Jul., 1966, pp. 271–272.

"Comments on Use of Exponential Dilution Flask in Calibration of Gas Analyzers", J. M. Sedlak et al., Analytical Chemistry, vol. 48, No. 13, Nov., 1976, pp. 2020–2022.

Primary Examiner—Tom Noland
Attorney, Agent, or Firm—Alvin H. Fritschler

[57] ABSTRACT

A calibration device utilizing a series of highly accurate mass flow controllers is provided for rapidly delivering ultra high purity calibration gas mixtures, and sample gas, to a gas analyzer at elevated temperature conditions. Steady flow rates are desirably provided to the highly sensitive analyzer. Valves exterior (20–25) and interior (3–5) to the heated compartment (9), heated by temperature controlled heater strips (9a), control the mixing of the reference gases with the sample gas and/or the flow of sample or calibration gas to the analyzer (16). The interior valves are diaphragm valves.

23 Claims, 6 Drawing Sheets

CALIBRATION FOR ULTRA HIGH PURITY GAS ANALYSIS

BACKGROUND OF THE INVENTION

1. Field of the Invention

The invention relates to ultra high purity gas analysis. More particularly, it relates to the calibrating of highly sensitive gas analysis equipment.

2. Description of the Prior Art

High purity gas applications, gas mixture standards are typically provided in cylinders at the parts per million (ppm) level. The semiconductor industry, however, requires ultra high purity (UHP) levels for gases used therein. This requirement arises from the need to decrease the dimensions of the line spacing for semiconductor devices. As the lines on semiconductor devices move closer together, impurities must be maintained in the low parts per billion (ppb) and even parts per trillion (ppt) range. The need for gas supplies with purity levels less than 1 ppb has driven industry to develop new analytical techniques for measuring gas purities. Recent advances in the gas analysis instrumentation art have provided users with the ability to examine lower concentration levels of impurities in main gas streams. The need to calibrate gas analysis instrumentation in the same range of impurities as would be found in the typical sample gas has led to increased demand for low concentration gas mixture standards. This need has occasioned the problem of obtaining a reliable gas standard for the calibration of such instrumentation. Gas mixtures supplied in cylinders or containers at the ppb or ppt levels are difficult to prepare and the reliability of the concentration is questionable. The reliability of a low concentration gas mixture is subject to question because of reactions occurring between the trace components of the mixture and the walls of the container. The adsorption/desorption of impurities onto all surfaces that come into contact with the gas presents a problem in measurements at low concentration levels. Such surfaces include regulators, valves, mass flow controllers, and transfer tubing runs, which deliver the calibration or sample gas to the analyzer. While it is difficult to know when an equilibrium has been reached with these components, this equilibrium is essential in order for the purity level of a gas to be confidently specified. Reactions can also occur at wetted surfaces, which can convert one impurity molecule into another, e.g. CO into $CO_2$.

The transfer of gases from one container to another also introduces an uncertainty in this regard. For instance the possibility of atmosphere leakage is present when such a transfer takes place. The measured weight of an impurity gas becomes vanishingly small when trying to produce low concentration standards in cylinders, and the impurity level of the balance gas plays an increasing role in determining the final concentration.

To overcome these problems, a gas delivery system must have the ability to deliver multilevel calibration gas and a sample gas without major disruption. The system should be simple in nature, with the lowest transfer volume and minimum number of components, and uncomplicated to operate. Such a system and the related method of calibration are needed to achieve the ever tighter specifications in the electronic gas industry.

It is an object of the invention to provide an improved calibration system and method for ultra high purity gas analysis.

With this and other objects in mind, the invention is hereinafter described in detail, the novel features thereof being particularly pointed out in the appended claims.

SUMMARY OF THE INVENTION

The gas blending system of the invention utilizes a series of highly accurate mass flow controllers capable of producing a stable gas mixture and of being used to generate a multipoint calibration curve in the ultra high purity, i.e. low ppb and ppt, range.

BRIEF DESCRIPTION OF THE INVENTION

The invention is hereinafter described in detail with reference to the accompanying drawings in which.

DETAILED DESCRIPTION OF THE INVENTION

The objects of the invention are accomplished using a system that produces steady flow rates of a dynamically prepared calibration gas mixture at the desired ultra-low concentration, providing a means for calibrating highly sensitive gas analysis equipment, such as an atmospheric pressure ionization mass spectrometer (APIMS). The system of the invention combines a purifier using a mass blending system operating at an elevated temperature to rapidly deliver UHP calibration gas for the calibration purposes of the invention. A reference gas, which is the same as the major constituent of the sample stream, is employed. A high concentration gas mixture is utilized in the process of the invention to generate the variable concentration calibration gases. By combining the appropriate flow rates, the process can be used to generate the desired calibration gas mixtures needed for the gas analysis system being calibrated.

Figure 1:
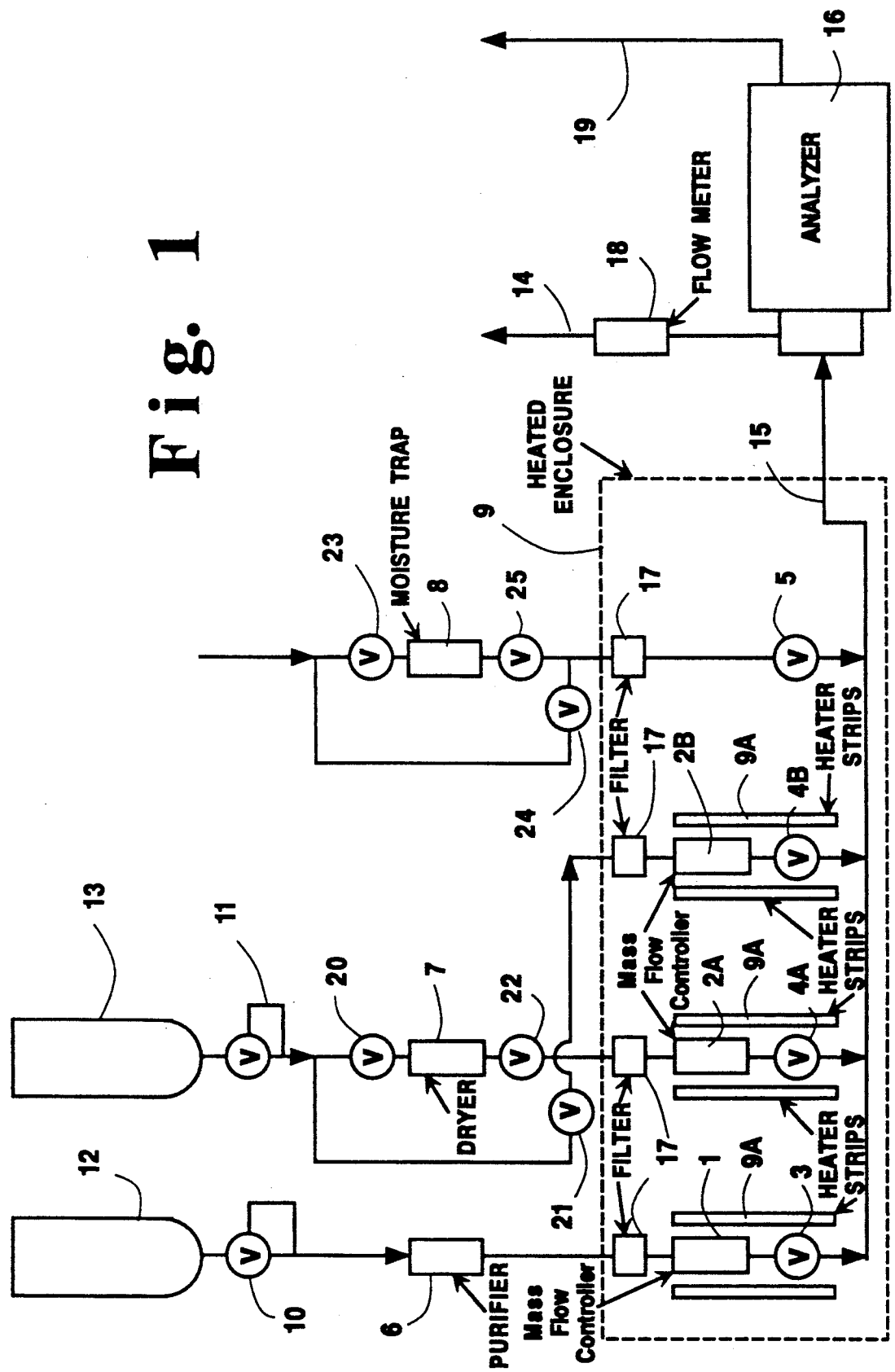
FIG. 1 is a schematic flow diagram of an embodiment of the calibration device of the invention.

In the embodiment shown in FIG. 1 of the drawings, mass flow controllers 1, 2A and 2B are employed, together with packless valves 3, 4A, 4B and 5, and electropolished all-welded tubings and fittings, which are based in an elevated temperature controlled, heated enclosure 9. Inlets to the system are supplied by a purified reference or diluent gas from cylinder 12, and a gas mixture of known impurity concentration supplied from cylinder 13. The mass flow controllers 1, 2A and 2B, typically operating at pressures under 100 psig, are selected to efficiently dilute flows from the high gas mixture cylinder 13 to the desired range, and to provide the needed flow for analyzer 16. The gas mixture from cylinder 13 is blended with the reference gas from cylinder 12 through the system to form the desired gas mixture concentrations. The invention also enables a sample gas to be introduced within the apparatus so as to minimize any disruption to analyzer 16. The exposure of any sampling components to atmospheric conditions is detrimental to the operation of any highly sensitive analyzer. The leak tight integrity of the system of the invention, its operation at elevated temperature, and the overall simplicity of the system overcome the problems commonly associated with the preparing of a reliable gas mixture at low concentrations.

The highly advantageous features of the invention, including its operation at elevated temperature, the simplicity of the system design, and the placement and sequence of operation of the flow controllers, valves and fittings are vital aspects of the system and its operation to achieve enhanced response time and overall calibration performance.

It will be understood that the high purity reference gas and a high concentration gas mixture must be selected to closely simulate the sample gas. For example, if the sample is nitrogen, the reference gas should also be nitrogen, and the high concentration gas mixture has nitrogen as its base gas. Such gases, normally supplied from a high pressure source, must be reduced in pressure by the use of a high purity pressure regulator. The regulator must be of the metal diaphragm type, which prevents diffusion of atmospheric contaminants therethrough and which utilizes high integrity, leak free connections. The reference gas is purified with a point-of-use purifier. This purifier can be of the heated metal getter type, which removes impurities through reliable chemical reactions to produce a high integrity reference gas.

The process of the invention requires particle free gases and, to assure this condition, inline filters are utilized to protect downstream components of the system, as such particles would otherwise detrimentally effect the performance of the mass flow controllers positioned downstream of the filters.

The process of adjusting flow rates to achieve the desired concentration mixtures is accomplished through the mass flow controller electronics module. The desired setpoint is entered into the system through a numeric key pad. The settings are determined through a combination of the high concentration gas mixture and the total flow rate requirements of the analyzer. These factors are taken into account when using a formula that ratios the flow rates of the reference gas and the high concentration gas mixture, which is multiplied by the high concentration gas mixture value to determine the final concentration, as illustrated below. A convenient process starting point is to determine the analyzers baseline response to the reference gas. This is accomplished by manipulating the appropriate shutoff valves located on the inlets of the manifold that supplies the analyzer with gas. Depending on the type of analysis desired, gas dryers with bypass capabilities are located in the high concentration gas mixture and the sample gas streams. These capabilities are essential for desired flexibility in the application of the analyzer to determine moisture concentrations in a gas or to eliminate the interferences that high concentrations of moisture would impose on other impurities in a sample.

As shown in said FIG. 1, the gas blending system of the invention employs high purity diluent or reference gas in cylinder 12, connected through pressure regulator 10 to purifier 6. Gas from the outlet of purifier 6 flows through, for example, a 10 micron particle filter 17, into mass flow controller 1, and then through diaphragm shutoff valve 3. Particle filters 17 serve to prevent any particles from damaging the mass flow controllers or diaphragm valves. Flow controllers 1 is sized in such a way as to meet the requirements of analyzer 16 and to allow for a bypass flow through line 14. A flowmeter 18 is located on bypass stream line 14 for monitoring the bypass flow rate. Flow controller 1, as desirably employed, has a full scale flow rate of 2 standard liters per minute (SLM), which is typical for an analyzer. This will be the reference gas for analyzer 16, and it is imperative to have the highest quality system components to ensure that a reliable reference reading is obtained. The reference gas minimizes the background interference in an analyzer's signal, giving a reference point upon which to base further analyses. All components after purifier 6 are electropolished stainless steel, including mass flow controllers 1, 2A and 2B. The leak tight integrity of mass flow controllers 1, 2A and 2B, and of diaphragm valves 3, 4A, 4B and 5, must be such as not to introduce any atmospheric contaminants into the system. Shutoff valves 3, 4A, 4B and 5, must also be free from cross port leakage. The leak specifications for the components used in the system of the invention are established for each embodiment. The distance between purifier 6 and mass flow controller 1 is kept to a minimum, e.g. less than about 12" of linear tubing run. Shutoff valve 3 supplies the reference gas, desirably, to an orbitally butt welded manifold 15 to which analyzer 16 is connected.

The construction of manifold 15 is such as to minimize its overall dimensions. This is achieved by utilizing special fittings that are compact in size and are designed to provide a smooth internal flow path. Such fittings, designed for UHP applications, are commercially available as, for example, the CAJUN ® Micro-Fit ® weld fittings made by CAJUN Company of Macedonia, Ohio.

Figure 3:
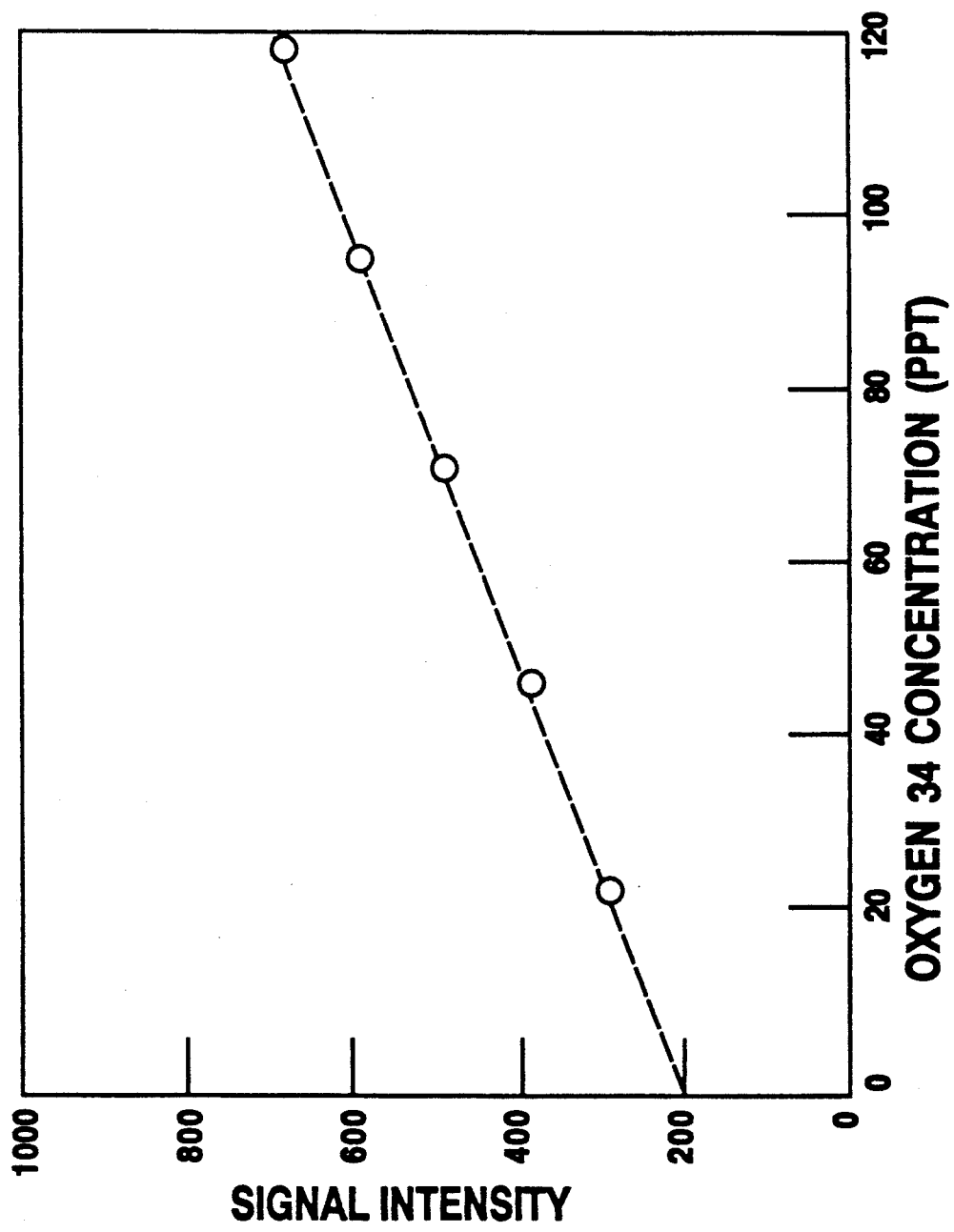
FIG. 3 is a calibration curve for oxygen at mass 34 based on data produced in the practice of the invention.

Filter means 17, flow controllers 1, 2A and 2B, diaphragm valves 3, 4A, 4B and 5, and, manifold 15 are housed inside temperature controlled, heated chamber 9. Mass flow controllers 1, 2A and 2B and the body of diaphragm valves 3, 4A, 4B and 5 are desirably mounted on an aluminum plate that is conveniently heated by temperature controlled heater strips, i.e. heater strips 9A. Efficient heat transfer takes place to maintain the components in a desired temperature range, i.e. about 60–80° C. The preferred temperature is about 70° C.±0.5° C. A more desirable operating temperature range, from the standpoint of moisture and other gas desorption, and hence of response time, would be about 80–150° C. However, the presently commercially available mass flow controllers are not functional above 80° C. It will be appreciated that temperature control is critical for stable operation of the system. Fluctuations in the temperature of the components will cause fluctuations in an analyzer's response to adsorption/desorption of contaminants. This point is illustrated in FIG. 3, which shows a fast response and increase in moisture signal with increase in temperature from 25° C. to 2,000° C.

The high concentration calibration gas mixture cylinder 13 is connected to pressure regulator 11, and then to moisture dryer 7 and filter means 17, and to at least one, preferably at least two, mass flow controllers, e.g. 2A and 2B and associated by-pass tubing. The multiple flow controllers 2A and 2B are used to improve the accuracy of the calibration gas mixture concentration. The process ranges for the flow controllers 2A and 2B are selected to provide the widest flow limits to achieve the desired gas mixture concentrations. For purposes of the calibration system of the invention, the range of flow controllers 2A and 2B are conveniently 0-100 cc/min and 0-1 cc/min, respectively, in relation to 0-2000 cc/min for reference gas flow controller 1. Each calibration gas mixture mass flow controller, i.e. 2A and 2B is connected to a diaphragm valve, i.e. to valves 4A and 4B, respectively, which feeds manifold 15 which in turn is connected to analyzer 16 which has vent line 19 extending therefrom. The sequence in which flow controllers 1, 2A and 2B are connected to manifold 15 is such as to establish quick response times and the operational functionality of the system. Thus, the order of sequencing must be such that the reference gas from cylinder 12 is furthest from the inlet to analyzer 16, with the larger calibration gas mass flow controller 2A being next in position, and with the smallest mass flow controller 2B for the gas from calibration gas mixture cylinder 13 being closest to said analyzer 16. The distance between each separate component is kept to a minimum, with the distance between each component being dictated by the size of the components and the ability to weld fittings together. In particular embodiments, the distance between separate components has been kept to less than 2". In any event, the components are positioned in close proximity to one another, with the distance therebetween being minimized.

As will be seen in FIG. 1, diaphragm valve 5, to which the sample gas can be introduced is also attached to manifold 15. The sample gas can be introduced directly into analyzer 16, or it can flow through moisture trap, or dryer, 8 prior to passage to manifold 15. Moisture trap 8 is commonly used in cases where the sample gas contains a large quantity of moisture. Such moisture will limit the use of a highly sensitive analyzer 16, such as an APIMS, for characterizing other impurities in the sample gas.

It should be noted that it is important to minimize the overall size of manifold 15 downstream of valves 3, 4A, 4B and 5 to provide the desired responsiveness of the gas blending system. Thus, the total internal volume of said manifold 15 is desirably less than about 10 cc. This low internal volume enables the system to be completely purged in less than one second. Dead legs, segments of a manifold that are not under flow conditions, and the like, would be a detriment to the responsiveness of the system and are to be kept to a minimum in practical commercial embodiments of the invention.

The operation of the system is through a changing of flow levels in the various flow controllers 1, 2A and 2B, to achieve the desired final concentrations. The reference gas flow can be generated by opening reference gas diaphragm valve 3 followed by the using of diaphragm valves 4A, 4B and 5 on the other ports of manifold 15. To generate a calibration gas mixture, the reference gas is used in combination with the high concentration gas mixture cylinder. The final concentration is determined by ratioing the reference gas flow rate to the high concentration gas mixture flow rate. The combination of the selected ranges of the mass flow controllers and the high concentration gas mixture cylinder values determine the range of concentrations that can be produced with the system. Sample calculations are shown below using a high concentration gas mixture of 500 ppb to produce calibration gases of 20 ppb and 0.25 ppb (250 ppt), with the final concentration (ppb) determined as follows:

$$\text{Final Concentration} = \frac{C_1 * Q_2}{Q_1 + Q_2}$$

where
$C_1$ = high concentration gas mixture (ppb),
$Q_1$ = reference gas flow rate (cc/min),
$Q_2$ = high concentration gas mixture flow rate (cc/min).

EXAMPLE 1

Final concentration of 20 ppb of impurity $$\text{Final concentration (ppb)} = \frac{50 \, ppb * 50 \, cc/min}{1,200 \, cc/min + 50 \, cc/min}$$

Final concentration (ppb) = 20 ppb.

EXAMPLE 2

Final concentration of 250 ppt of impurity $$\text{Final concentration (ppb)} = \frac{500 \, ppt * 1 \, cc/min}{1,999 \, cc/min + 1 \, cc/min}$$

Final concentration (ppb) = 250 ppt.

Figure 4:
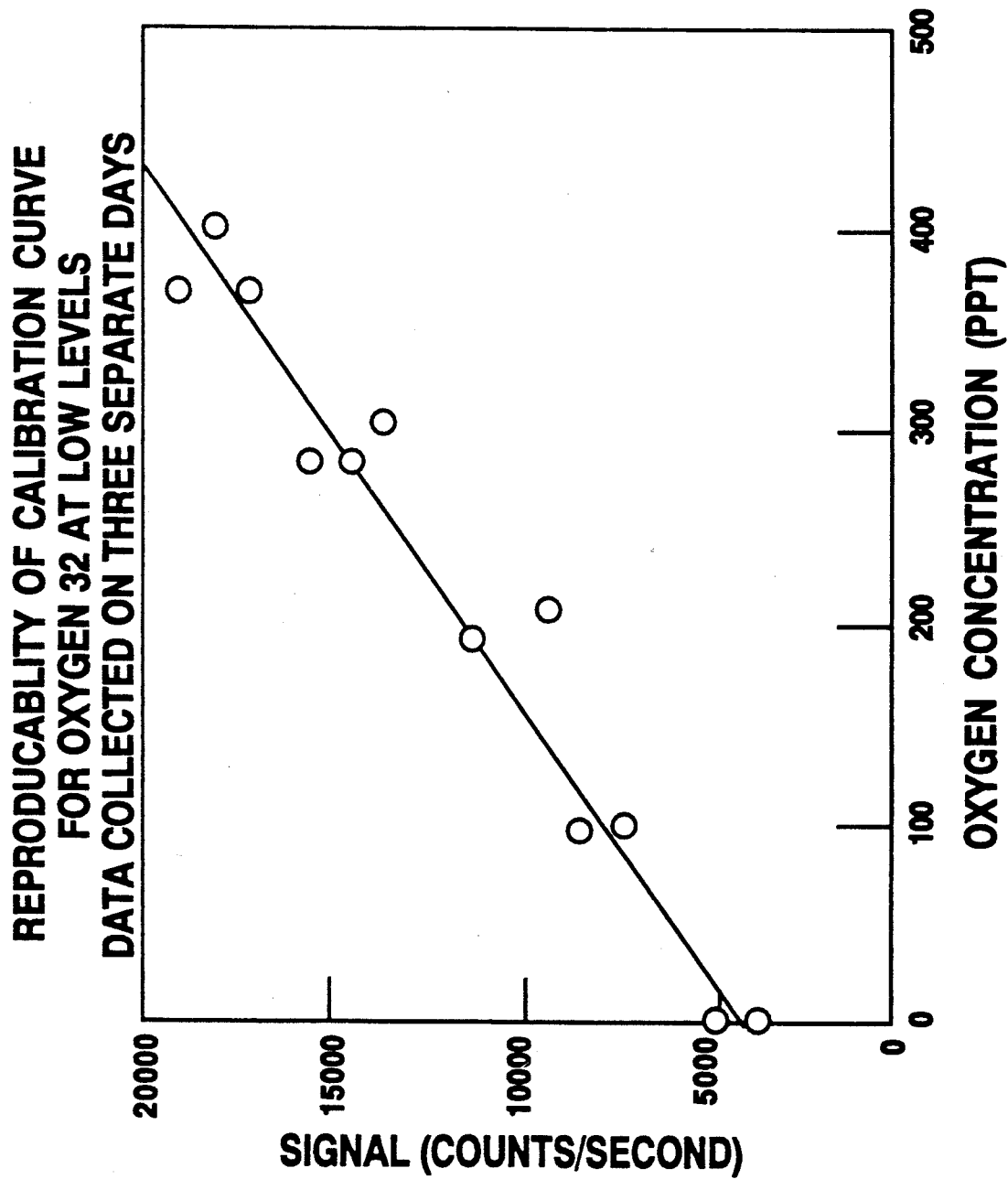
FIG. 4 is a calibration curve for oxygen at mass 32 based on data collected on three separate days in the practice of the invention.
Figure 5:
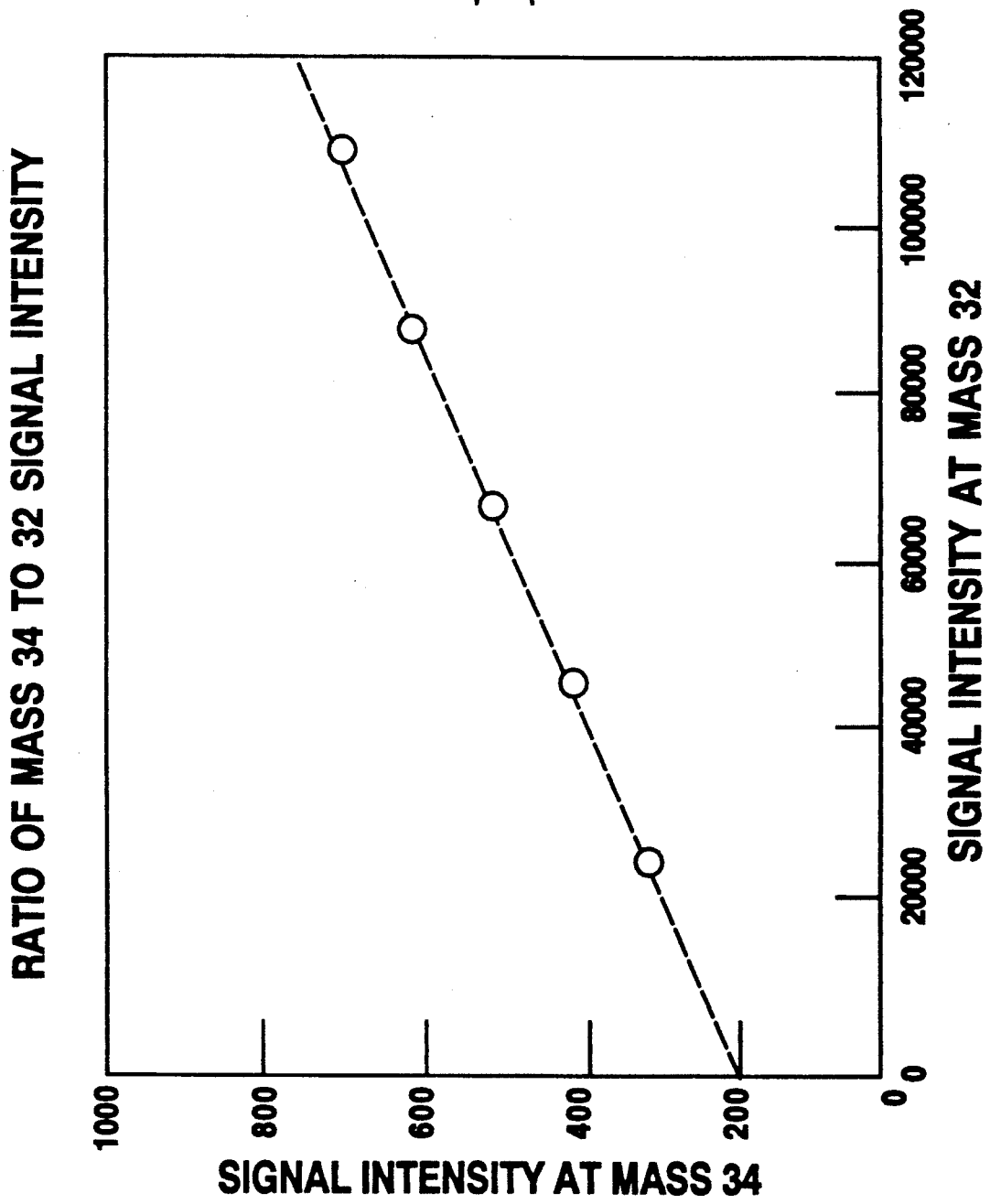
FIG. 5 is a graph of the ratio of mass 34 to 32 signal intensity based on data obtained in the Practice of the invention.
Figure 6:
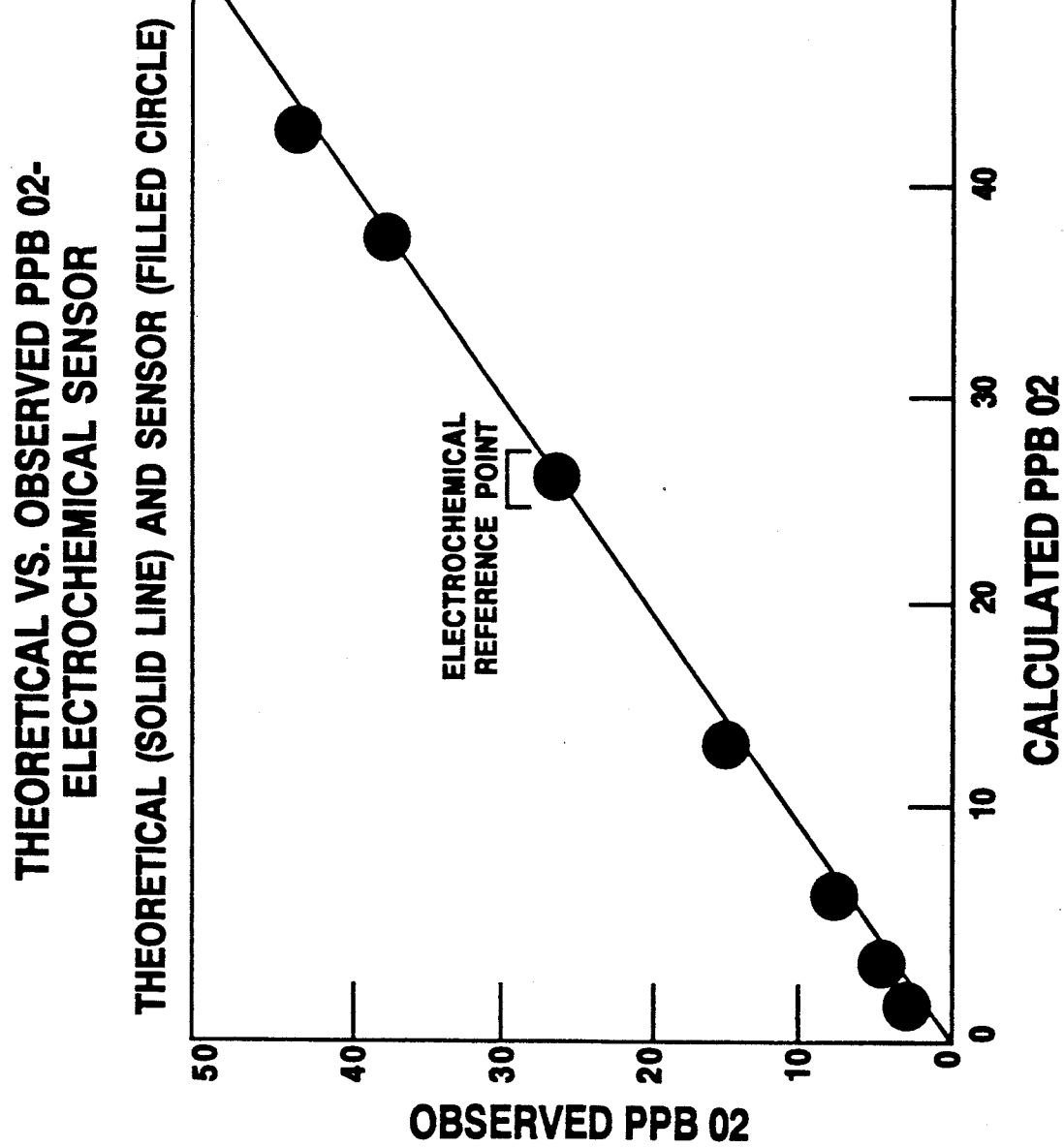
FIG. 6 is a graph showing the conformance of the observed ppb oxygen using an electrochemical sensor with the theoretical ppb oxygen.

FIGS. 3, 4 and 5 demonstrate the capabilities of the invention. The data presented was collected in a highly sensitive APIMS analyzer, which is capable of measuring these low concentrations. FIG. 3 demonstrates the ability to control concentration changes in the low ppt range. Each point in the graph represents a change of about 20 ppt. FIG. 4 demonstrates the reproducibility of the system. The graph contains points collected over three separate days. Those skilled in the art will appreciate that it is necessary for a calibration system to be reproducible. The finite signal intensity at zero concentration shown in FIGS. 3 and 4 is a result of background interferences and a minor contribution from impurities in the reference gas. FIG. 5 demonstrates the ability of the calibration system to deliver a calibration gas without affecting the composition. The isotropic ratio of an element is well known. The predominant isotopes for oxygen are mass 16 and mass 18. The formation of an oxygen molecule can bring together one of each of these atoms to form oxygen-34. The natural abundance ratio of oxygen-34 to oxygen-32 is 0.00407. The slope determined by FIG. 6 is 0.00478, which represents very good conformance with the theoretical ratio.

The invention was tested against a process analyzer, which has the capability of generating its own calibration through an electrical signal. This calibration is directly traceable to first principles, i.e. Faraday's Law. The lower detection limit of this analyzer is 2 ppb. FIG. 6 is a representation of this direct comparison. The graph illustrates the accuracy and linearity of the invention through this independent verification check.

The invention overcomes many of the problems inherent in prior techniques used for the production of calibration gas mixtures. The direct production of calibration gas mixtures in cylinders is limited to a lower concentration level of approximately 1 ppm by cylinder wall interactions with impurities. The system of the invention is capable of generating calibration gases to a lower concentration level of approximately 10 ppt (0.00001 ppm). Prior dilution systems have been utilized for the production of lower concentration ppb range calibration gas mixtures. Limitations in prior systems to produce calibration gases over a wide range through the use of single flow elements in the high concentration calibration gas have hampered the production of ppt concentration calibration gases. The need to achieve ppt calibration gas has required the use of double dilution techniques in prior systems, which adds components to the system. Such additional components detrimentally impact the response time of the prior systems. The invention achieves these lower concentration levels though simpler design and elevated temperature operations. The improved operation of the system of the invention over prior dilution systems also improves the accuracy of the final mixture concentration. This can be determined from the accuracy of the mass flow controllers utilized in particular embodiments of the invention.

Figure 2:
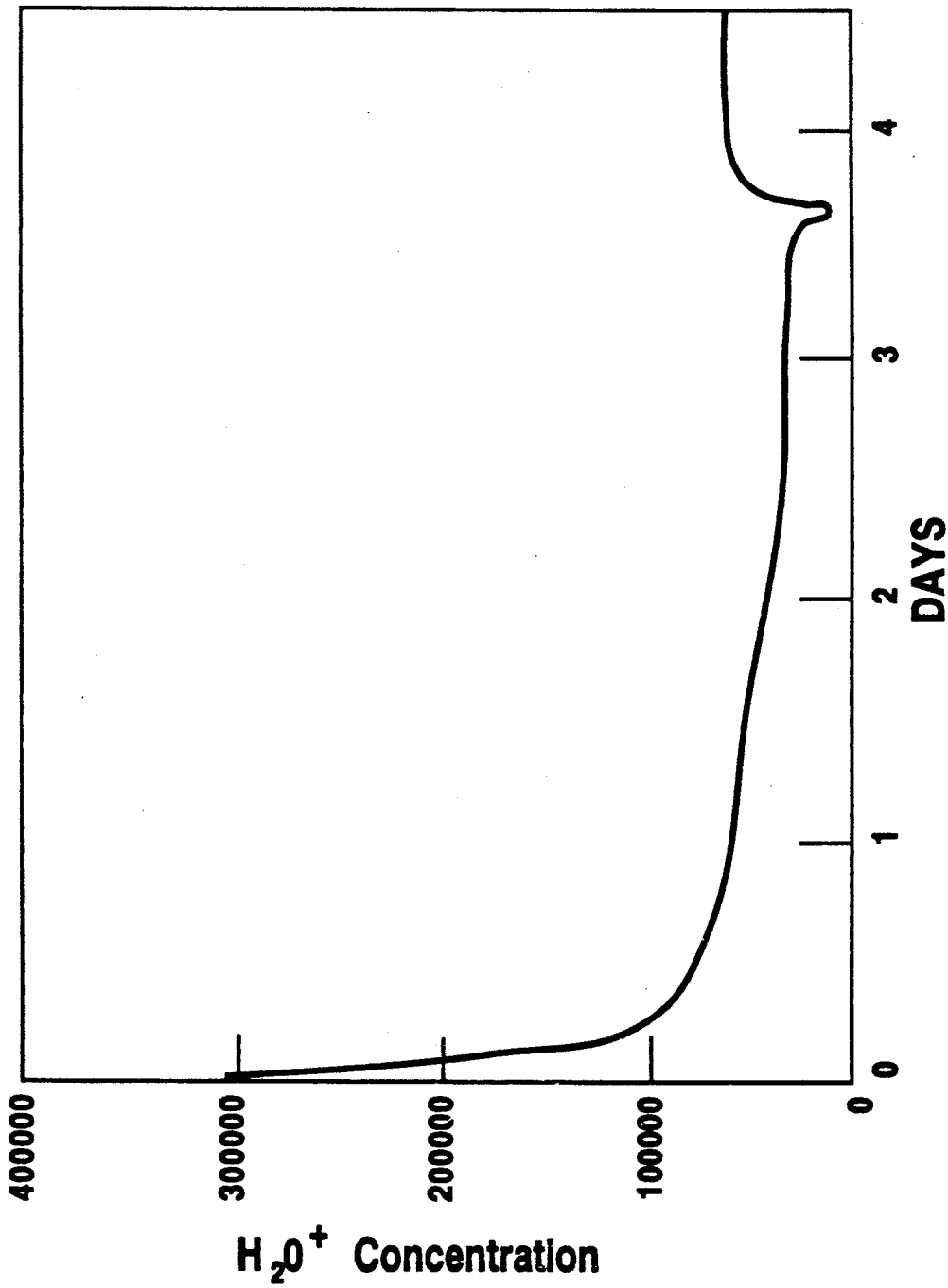
FIG. 2 is a plot showing the temperature effect on moisture analysis based on data produced in the practice of the invention.

A significant attribute of the invention is its operation at elevated temperatures. The controlled heating of the system provides a more stable system, and also decreases the response time of the system. The graph shown in FIG. 2 illustrates the effect of heating the system components. After four days of purging a $\frac{1}{8}''$ stainless steel tube, heat was applied to the tube, and additional moisture was observed coming off the tube. This is demonstrated clearly by the rise in signal displayed in said FIG. 2. Ambient temperature fluctuations could detrimentally effect the stability of a highly sensitive analyzer, such as an APIMS. The importance of response time is manifested in the ability to generate low level ppt gas calibration mixtures. If the components desorb contaminants over several days, low ppt readings would be impossible to achieve.

The ability to introduce a sample gas within the manifold is advantageous in not disrupting the analyzer. The time delay for switching from one sample to a calibration would severely impair the functionality of an analyzer in the low ppb and ppt range. In the system of the invention, the number of components will be seen to be held to a minimum. By so minimizing the number of components, the necessary equilibrium time to achieve a steady concentration is minimized. The elimination of possible leak sources is also an advantage in the reducing, to a minimum, the number of components in the system. The highest integrity that can be achieved is through direct welding of components. Since it is not always possible, the use of face seal fittings has been found acceptable. The internal volume of the system can be reduced by utilizing orbitally butt welded connections and face seal fittings. The smaller the internal volume, the faster the concentration equilibrium will take place. Compact design is another primary driving force with respect to the subject system. To achieve the low concentration levels needed for sensitive analyzers, multiple flow controllers are utilized. This improves the accuracy of the mixture generated. The errors for mass flow controllers are relative to the full scale range of the mass flow controller, 1-2% of the full scale range being typical. The reproducibility of mass flow controllers is substantially better, typically in the range of 0.2%, so that, once set, the mass flow controller will return to the same flow level each time. By decreasing the full scale range of a mass flow controller, the absolute error will be substantially reduced, thereby improving the ability to generate low concentration calibration gas mixtures.

The high concentration gas flow controllers have a far greater impact on the final mixture concentration than the reference gas flow controller does because the reference gas flow controller full scale value is at least 20 times greater than the high concentration calibration gas flow controllers. Without the use of multiple flow controllers, it would not be possible to generate accurately, or to generate a wide range of calibration gas mixtures.

It will be understood from the above that the method of producing low concentration gas mixtures using the calibration device of the invention, as illustrated in FIG. 1, comprises introducing reference gas from cylinder 12 through high purity pressure regulator 10 for gas pressure reduction and stability. The resulting regulated reference gas flows to purifier 6, and continues through filter 17 for particulate removal. The reference gas then passes to the inlet of mass flow controlling device 1 to precisely control its outlet flow.

A high concentration gas mixture from container 13 is passed to high purity regulator 11, which is likewise used to reduce the gas pressure and maintain a stable pressure in the line. The high concentration gas mixture exiting regulator 11 is directed to optional gas dryer 7, or it can bypass dryer 7 through manipulation of valves 20, 21 and 22, and enter particulate filter 17. The gas flow from filter 17 enters multiple pass mass flow controllers 2A and 2B, with two such mass flow controllers being a minimum requirement for purposes of the invention.

The system of the invention is adapted for the introduction of a sample gas stream. This sample gas can either be directed into filter 17, or it can flow first through dryer 8, through manipulation of valves 23, 24 and 25, and then into filter 17.

The effluents from the combined mass flow controllers, i.e. 1, 2A and 2B, and the sample gas streams are introduced into manifold 15 through high purity diaphragm valves 3, 4A, 4B and 5. The mass flow controllers are selected in such a fashion as to provide sufficient flow to the outlet so that analyzer 16 connected to the outlet of manifold 15 will experience an excess flow as measured by flowmeter 18. The flow adjustment of the mass flow controllers is a determining factor in the method of operation to set the final calibration gas mixture concentration. The method of producing low concentration gas mixtures using the system of the invention comprises:

(1) pressure reduction of the reference gas source by use of a high purity regulator;

(2) conditioning the reference gas with a point of use purifier;

(3) filtering the reference gas;

(4) precisely controlling the flow rates of the reference gas using a mass flow controlling device;

(5) pressure reduction of the high concentration gas mixture by use of a high purity regulator;

(6) providing the option of conditioning the high concentration gas mixture through the gas dryer, or bypassing said gas dryer;

(7) filtering the high concentration gas mixture;

(8) precisely controlling flow rates of the high concentration gas mixture utilizing at least two mass flow controlling devices;

(9) providing for positive shutoff of the high concentration gas mixture by the preferred use of diaphragm sealed valves;

(10) diluting the high concentration gas mixture with the reference gas to achieve the desired mixture by manipulation of the mass flow controlling devices; and

(11) supplying the final gas mixture in sufficient quantities to the analyzer to satisfy the needs thereof, while allowing for an excess bypass flow.

The invention will be seen to provide a highly desirable calibration device for use in generating calibration gases in the low ppb/ppt range. As such, it desirably advances the art in providing an advantageous means for satisfying the ever tighter specifications required by the electronic gas industry.

We claim:

1. A calibration system for ultra high purity gas analysis comprising:
   (a) container means for a reference gas;
   (b) container means for a high concentration gas mixture;
   (c) point-of-use purifier means adapted to remove impurities from said reference gas;
   (d) a heated compartment adapted to maintain a controlled elevated temperature and minimize fluctuations therein;
   (e) filter means for separately filtering said reference gas and said high concentration gas mixture to remove particles therefrom, said filter means being positioned within said heated compartment,
   (f) mass flow controller means for separately controlling the flow of said reference gas and said high concentration gas mixture, said mass flow controller means being positioned within said heated compartment and being essentially leak tight to prevent the introduction of atmospheric contaminants into either the reference gas or the high concentration gas mixture, said mass flow controller means for the high concentration gas mixture comprising at least one mass flow controller means;
   (g) manifold means positioned within said heated compartment and being adapted to receive gas from said mass flow controller means for passage to a means for the analysis thereof, said manifold means having inlets therein for the passage of the reference gas and said high concentration gas mixture from said mass flow controller means to said manifold means, and shutoff valves to control the flow of said gases from the mass flow controller means to said manifold means, said shutoff valves being essentially leak tight to prevent the introduction of atmospheric contaminants into the reference gas or into the high concentration gas mixture passing from any of said mass flow controller means, all tubing and fittings within the heated compartment being electropolished, all said components therein comprising electropolished stainless steel; and
   (h) gas analyzer means capable of measuring gas purity in either the high purity or low ppm/ppt range, whereby the system, operating at elevated temperature, having leak tight integrity and design simplicity enables reliable gas mixtures to be prepared in the ultra high purity range for variable concentration gas calibration purposes.

2. The system of claim 1 in which said mass flow controller means for the high concentration gas mixture comprises at least two mass flow controller means of varying flow limits.

3. The system of claim 2 in which said mass flow controller means for the high concentration gas mixture comprises two mass flow controller means.

4. The system of claim 3 in which the flow capacity range of one mass flow controller means for the high concentration gas mixture is in the range of 0 to 100 cc/min and the flow capacity range of said second mass flow controller means for said high concentration gas mixture is from about 0-1 cc/min.

5. The system of claim 4 in which the flow capacity range of the mass flow controller means for the reference gas is in the range of from 0 to 2,000 cc/min.

6. The system of claim 1 and including dryer means for drying said high concentration gas mixture prior to its passage to said filter means.

7. The system of claim 6 in which said filter means for the high concentration gas mixture comprises separate means for each portion of said mixture passing to separate mass flow controller means.

8. The system of claim 1 in which said heated compartment is adapted to maintain a controlled temperature within the range of from about 60° C. to about 80° C.

9. The system of claim 8 in which said heated compartment is adapted to maintain a controlled temperature of about 70° C.±0.5° C.

10. The system of claim 1 in which said shutoff valves comprise diaphragm valves.

11. The system of claim 1 and including pressure regulator means for reducing the pressure of said reference gas and of said high concentration gas mixture upon discharge from said separate container means therefor, said regulator means being essentially leak tight to prevent the introduction of atmospheric contaminants into either the reference gas or said high concentration gas mixture.

12. The system of claim 11 in which said pressure regulator means comprises metal diaphragm type pressure regulator means to preclude diffusion of atmospheric contaminants into either the reference gas or the high concentration gas mixture.

13. The system of claim 1 and including conduit means for introducing sample gas to separate filter means positioned within the heated compartment to remove particles from said sample gas, said manifold means having an inlet therein for the passage of the sample gas from said filter means to said manifold means, and including shutoff valve means to control the flow of the sample gas from said filter means to said manifold means, said shutoff valve being essentially leak tight to prevent the introduction of atmospheric contaminants into the sample gas.

14. The system of claim 13 in which said shutoff valve means to control the flow of sample gas from the filter means to said manifold means comprises a diaphragm valve.

15. The system of claim 1 and including bypass flow conduit means for diverting gas passing to said gas analyzer means.

16. The system of claim 15 and including flowmeter means positioned in said bypass flow conduit means.

17. The system of claim 1 in which the inlets for the manifold means are positioned such that the inlet for reference gas is furthest from said gas analyzer means, the inlet for gas from the larger higher concentration gas mixture mass controller means is positioned next thereto, and the inlet for gas from the smallest higher concentration gas mixture mass flow controller means is positioned closest to said gas analyzer means.

18. The system of claim 17 in which said mass flow controller means for the high concentration gas mixture comprises two mass flow controller means.

19. The system of claim 1 in which the separate components are positioned in close proximity to one another, consistent with the size of said components and the ability to weld component fittings together.

20. The system of claim 19 in which the distance between components is less than about 2".

21. The system of claim 1 in which the total internal volume of said manifold means is less than about 10 cc, thereby enabling the system to be completely purged in less than about 1 second.

22. The system of claim 1 in which said gas analyzer means comprises an atmospheric pressure ionization mass spectrometer.

23. The system of claim 1 in which the distance between said point-of-use purifier means and said mass flow controller means for controlling the flow of the reference gas is less than about 12".

* * * * *